(12) United States Patent
Stopek

(10) Patent No.: US 8,740,904 B2
(45) Date of Patent: Jun. 3, 2014

(54) SEAL ANCHOR INTRODUCER INCLUDING BIASING MEMBER

(75) Inventor: Joshua Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 33 days.

(21) Appl. No.: 12/938,691

(22) Filed: Nov. 3, 2010

(65) Prior Publication Data

US 2011/0124969 A1 May 26, 2011

Related U.S. Application Data

(60) Provisional application No. 61/263,906, filed on Nov. 24, 2009.

(51) Int. Cl.
*A61B 17/56* (2006.01)

(52) U.S. Cl.
USPC .......................................................... 606/64

(58) Field of Classification Search
CPC ...... A61B 17/02; A61B 1/32; A61B 17/0218; A61B 17/0293; A61B 17/0206; A61B 17/3421; A61B 17/3431; A61B 17/3439; A61B 2017/3423; A61B 2017/3443; A61B 2017/3439
USPC ....................... 600/201–246; 623/23.64–23.7
See application file for complete search history.

(56) References Cited

U.S. PATENT DOCUMENTS

| | | | |
|---|---|---|---|
| 3,738,365 A * | 6/1973 | Schulte | ............................. 604/8 |
| 4,016,884 A | 4/1977 | Kwan-Gett | |
| 4,112,932 A | 9/1978 | Chiulli | |
| 4,183,357 A | 1/1980 | Bentley et al. | |
| 4,402,683 A | 9/1983 | Kopman | |
| 4,653,476 A | 3/1987 | Bonnet | |
| 4,863,430 A | 9/1989 | Klyce et al. | |
| 4,863,438 A | 9/1989 | Gauderer et al. | |
| 5,073,169 A | 12/1991 | Raiken | |
| 5,082,005 A | 1/1992 | Kaldany | |
| 5,159,921 A | 11/1992 | Hoover | |
| 5,176,697 A | 1/1993 | Hasson et al. | |
| 5,183,471 A | 2/1993 | Wilk | |
| 5,192,301 A | 3/1993 | Kamiya et al. | |
| 5,242,409 A | 9/1993 | Buelna | |
| 5,242,415 A | 9/1993 | Kantrowitz et al. | |
| 5,257,973 A | 11/1993 | Villasuso | |
| 5,257,975 A | 11/1993 | Foshee | |
| 5,269,772 A | 12/1993 | Wilk | |
| 5,312,391 A | 5/1994 | Wilk | |
| 5,330,486 A | 7/1994 | Wilk | |
| 5,334,143 A | 8/1994 | Carroll | |
| 5,345,927 A | 9/1994 | Bonutti | |

(Continued)

FOREIGN PATENT DOCUMENTS

| | | |
|---|---|---|
| EP | 0807416 B1 | 11/1997 |
| EP | 0950376 | 10/1999 |

(Continued)

*Primary Examiner* — Mary Hoffman

(57) ABSTRACT

A seal anchor member has opposing ends that define a longitudinal axis. The seal anchor member is adapted to transition between an expanded condition and a compressed condition to facilitate securing of the seal anchor member within a tissue tract in a substantially sealed relationship. The seal anchor member includes a biasing member positioned along the longitudinal axis. The biasing member is configured and adapted to facilitate the transition between the expanded and compressed conditions. The seal anchor member further includes at least one lumen extending through the seal anchor member for slidably receiving a surgical instrument.

14 Claims, 3 Drawing Sheets

(56) References Cited

U.S. PATENT DOCUMENTS

| | | | |
|---|---|---|---|
| 5,366,478 A | 11/1994 | Brinkerhoff et al. | |
| 5,375,588 A | 12/1994 | Yoon | |
| 5,391,156 A | 2/1995 | Hildwein et al. | |
| 5,395,367 A | 3/1995 | Wilk | |
| 5,437,683 A | 8/1995 | Neumann et al. | |
| 5,460,170 A | 10/1995 | Hammerslag | |
| 5,480,410 A | 1/1996 | Cuschieri et al. | |
| 5,490,843 A | 2/1996 | Hildwein et al. | |
| 5,507,758 A | 4/1996 | Thomason et al. | |
| 5,511,564 A | 4/1996 | Wilk | |
| 5,514,133 A | 5/1996 | Golub et al. | |
| 5,514,153 A | 5/1996 | Bonutti | |
| 5,522,790 A * | 6/1996 | Moll et al. | 600/204 |
| 5,522,791 A | 6/1996 | Leyva | |
| 5,524,644 A | 6/1996 | Crook | |
| 5,540,648 A | 7/1996 | Yoon | |
| 5,545,179 A | 8/1996 | Williamson, IV | |
| 5,601,581 A | 2/1997 | Fogarty et al. | |
| 5,634,911 A | 6/1997 | Hermann et al. | |
| 5,634,937 A | 6/1997 | Mollenauer et al. | |
| 5,649,550 A | 7/1997 | Crook | |
| 5,651,771 A | 7/1997 | Tangherlini et al. | |
| 5,653,705 A | 8/1997 | de la Torre et al. | |
| 5,672,168 A | 9/1997 | de la Torre et al. | |
| 5,683,378 A | 11/1997 | Christy | |
| 5,685,857 A | 11/1997 | Negus et al. | |
| 5,713,858 A | 2/1998 | Heruth et al. | |
| 5,713,869 A | 2/1998 | Morejon | |
| 5,728,103 A | 3/1998 | Picha et al. | |
| 5,730,748 A | 3/1998 | Fogarty et al. | |
| 5,735,791 A | 4/1998 | Alexander, Jr. et al. | |
| 5,741,298 A | 4/1998 | MacLeod | |
| 5,782,817 A | 7/1998 | Franzel et al. | |
| 5,795,290 A | 8/1998 | Bridges | |
| 5,797,888 A * | 8/1998 | Yoon | 604/530 |
| 5,803,921 A | 9/1998 | Bonadio | |
| 5,810,712 A | 9/1998 | Dunn | |
| 5,813,409 A | 9/1998 | Leahy et al. | |
| 5,830,191 A | 11/1998 | Hildwein et al. | |
| 5,836,871 A | 11/1998 | Wallace et al. | |
| 5,842,971 A | 12/1998 | Yoon | |
| 5,848,992 A | 12/1998 | Hart et al. | |
| 5,853,417 A | 12/1998 | Fogarty et al. | |
| 5,857,461 A | 1/1999 | Levitsky et al. | |
| 5,865,817 A | 2/1999 | Moenning et al. | |
| 5,871,474 A | 2/1999 | Hermann et al. | |
| 5,876,413 A | 3/1999 | Fogarty et al. | |
| 5,894,843 A | 4/1999 | Benetti et al. | |
| 5,899,208 A | 5/1999 | Bonadio | |
| 5,899,913 A | 5/1999 | Fogarty et al. | |
| 5,904,703 A | 5/1999 | Gilson | |
| 5,906,577 A | 5/1999 | Beane et al. | |
| 5,916,198 A | 6/1999 | Dillow | |
| 5,941,898 A | 8/1999 | Moenning et al. | |
| 5,951,588 A | 9/1999 | Moenning | |
| 5,957,913 A | 9/1999 | de la Torre et al. | |
| 5,964,781 A | 10/1999 | Mollenauer et al. | |
| 5,976,079 A * | 11/1999 | Volz et al. | 600/209 |
| 5,976,174 A * | 11/1999 | Ruiz | 606/213 |
| 5,997,515 A | 12/1999 | de la Torre et al. | |
| 6,017,355 A | 1/2000 | Hessel et al. | |
| 6,018,094 A | 1/2000 | Fox | |
| 6,024,736 A | 2/2000 | de la Torre et al. | |
| 6,033,426 A | 3/2000 | Kaji | |
| 6,033,428 A | 3/2000 | Sardella | |
| 6,042,573 A | 3/2000 | Lucey | |
| 6,048,309 A | 4/2000 | Flom et al. | |
| 6,059,816 A | 5/2000 | Moenning | |
| 6,068,639 A | 5/2000 | Fogarty et al. | |
| 6,077,288 A | 6/2000 | Shimomura et al. | |
| 6,086,603 A | 7/2000 | Termin et al. | |
| 6,099,506 A | 8/2000 | Macoviak et al. | |
| 6,110,154 A | 8/2000 | Shimomura et al. | |
| 6,142,936 A | 11/2000 | Beane et al. | |
| 6,171,282 B1 | 1/2001 | Ragsdale | |
| 6,197,002 B1 | 3/2001 | Peterson | |
| 6,217,555 B1 | 4/2001 | Hart et al. | |
| 6,228,063 B1 | 5/2001 | Aboul-Hosn | |
| 6,238,373 B1 | 5/2001 | de la Torre et al. | |
| 6,241,768 B1 | 6/2001 | Agarwal et al. | |
| 6,254,534 B1 | 7/2001 | Butler et al. | |
| 6,264,604 B1 | 7/2001 | Kieturakis et al. | |
| 6,315,770 B1 | 11/2001 | de la Torre et al. | |
| 6,319,246 B1 | 11/2001 | de la Torre et al. | |
| 6,371,968 B1 | 4/2002 | Kogasaka et al. | |
| 6,382,211 B1 | 5/2002 | Crook | |
| 6,423,036 B1 | 7/2002 | Van Huizen | |
| 6,440,061 B1 | 8/2002 | Wenner et al. | |
| 6,440,063 B1 | 8/2002 | Beane et al. | |
| 6,443,957 B1 | 9/2002 | Addis | |
| 6,447,489 B1 | 9/2002 | Peterson | |
| 6,450,983 B1 | 9/2002 | Rambo | |
| 6,454,783 B1 | 9/2002 | Piskun | |
| 6,464,686 B1 | 10/2002 | O'Hara et al. | |
| 6,468,292 B1 | 10/2002 | Mollenauer et al. | |
| 6,488,620 B1 | 12/2002 | Segermark et al. | |
| 6,488,692 B1 | 12/2002 | Spence et al. | |
| 6,527,787 B1 | 3/2003 | Fogarty et al. | |
| 6,551,270 B1 | 4/2003 | Bimbo et al. | |
| 6,558,371 B2 | 5/2003 | Dorn | |
| 6,578,577 B2 | 6/2003 | Bonadio et al. | |
| 6,582,364 B2 | 6/2003 | Butler et al. | |
| 6,589,167 B1 | 7/2003 | Shimomura et al. | |
| 6,613,952 B2 | 9/2003 | Rambo | |
| 6,623,426 B2 | 9/2003 | Bonadio et al. | |
| 6,669,674 B1 | 12/2003 | Macoviak et al. | |
| 6,676,639 B1 | 1/2004 | Ternström | |
| 6,706,050 B1 | 3/2004 | Giannadakis | |
| 6,723,044 B2 | 4/2004 | Pulford et al. | |
| 6,723,088 B2 | 4/2004 | Gaskill, III et al. | |
| 6,725,080 B2 | 4/2004 | Melkent et al. | |
| 6,800,084 B2 | 10/2004 | Davison et al. | |
| 6,814,078 B2 | 11/2004 | Crook | |
| 6,837,893 B2 | 1/2005 | Miller | |
| 6,840,946 B2 | 1/2005 | Fogarty et al. | |
| 6,840,951 B2 | 1/2005 | de la Torre et al. | |
| 6,846,287 B2 | 1/2005 | Bonadio et al. | |
| 6,863,674 B2 | 3/2005 | Kasahara et al. | |
| 6,878,110 B2 | 4/2005 | Yang et al. | |
| 6,890,295 B2 | 5/2005 | Michels et al. | |
| 6,913,609 B2 | 7/2005 | Yencho et al. | |
| 6,916,310 B2 | 7/2005 | Sommerich | |
| 6,916,331 B2 | 7/2005 | Mollenauer et al. | |
| 6,929,637 B2 | 8/2005 | Gonzalez et al. | |
| 6,939,296 B2 | 9/2005 | Ewers et al. | |
| 6,945,932 B1 | 9/2005 | Caldwell et al. | |
| 6,958,037 B2 * | 10/2005 | Ewers et al. | 600/208 |
| 6,972,026 B1 | 12/2005 | Caldwell et al. | |
| 6,991,602 B2 | 1/2006 | Nakazawa et al. | |
| 6,997,909 B2 | 2/2006 | Goldberg | |
| 7,001,397 B2 | 2/2006 | Davison et al. | |
| 7,008,377 B2 | 3/2006 | Beane et al. | |
| 7,014,628 B2 | 3/2006 | Bousquet | |
| 7,033,319 B2 | 4/2006 | Pulford et al. | |
| 7,033,387 B2 * | 4/2006 | Zadno-Azizi et al. | 623/1.24 |
| 7,052,454 B2 | 5/2006 | Taylor | |
| 7,056,321 B2 | 6/2006 | Pagliuca et al. | |
| 7,077,852 B2 | 7/2006 | Fogarty et al. | |
| 7,081,089 B2 | 7/2006 | Bonadio et al. | |
| 7,100,614 B2 | 9/2006 | Stevens et al. | |
| 7,101,353 B2 | 9/2006 | Lui et al. | |
| 7,104,981 B2 | 9/2006 | Elkins et al. | |
| 7,153,261 B2 | 12/2006 | Wenchell | |
| 7,163,510 B2 | 1/2007 | Kahle et al. | |
| 7,192,436 B2 | 3/2007 | Sing et al. | |
| 7,195,590 B2 | 3/2007 | Butler et al. | |
| 7,214,185 B1 | 5/2007 | Rosney et al. | |
| 7,217,277 B2 | 5/2007 | Parihar et al. | |
| 7,223,257 B2 | 5/2007 | Shubayev et al. | |
| 7,223,278 B2 | 5/2007 | Davison et al. | |
| 7,235,084 B2 | 6/2007 | Skakoon et al. | |
| 7,238,154 B2 | 7/2007 | Ewers et al. | |
| 7,276,075 B1 | 10/2007 | Callas et al. | |
| 7,294,103 B2 | 11/2007 | Bertolero et al. | |

(56) References Cited

U.S. PATENT DOCUMENTS

| | | |
|---|---|---|
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,445,597 B2 | 11/2008 | Butler et al. |
| 7,452,363 B2 | 11/2008 | Ortiz |
| 7,473,221 B2 | 1/2009 | Ewers et al. |
| 7,540,839 B2 | 6/2009 | Butler et al. |
| 7,559,893 B2 | 7/2009 | Bonadio et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,798,898 B2 | 9/2010 | Luciano, Jr. et al. |
| 8,257,251 B2 * | 9/2012 | Shelton et al. ............ 600/206 |
| 2001/0037053 A1 | 11/2001 | Bonadio et al. |
| 2002/0038077 A1 | 3/2002 | de la Torre et al. |
| 2002/0055714 A1 | 5/2002 | Rothschild |
| 2002/0183594 A1 | 12/2002 | Beane et al. |
| 2003/0014076 A1 | 1/2003 | Mollenauer et al. |
| 2003/0135091 A1 | 7/2003 | Nakazawa et al. |
| 2003/0236549 A1 | 12/2003 | Bonadio et al. |
| 2004/0049099 A1 * | 3/2004 | Ewers et al. ............ 600/206 |
| 2004/0092795 A1 | 5/2004 | Bonadio et al. |
| 2004/0092796 A1 | 5/2004 | Butler et al. |
| 2004/0111061 A1 | 6/2004 | Curran |
| 2004/0138529 A1 | 7/2004 | Wiltshire et al. |
| 2004/0167543 A1 | 8/2004 | Mazzocchi et al. |
| 2004/0267096 A1 | 12/2004 | Caldwell et al. |
| 2005/0020884 A1 | 1/2005 | Hart et al. |
| 2005/0043592 A1 | 2/2005 | Boyd et al. |
| 2005/0070935 A1 | 3/2005 | Ortiz |
| 2005/0096695 A1 | 5/2005 | Olich |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0241647 A1 | 11/2005 | Nguyen et al. |
| 2005/0288558 A1 | 12/2005 | Ewers et al. |
| 2006/0020241 A1 | 1/2006 | Piskun et al. |
| 2006/0049317 A1 | 3/2006 | Reutenauer et al. |
| 2006/0084842 A1 | 4/2006 | Hart et al. |
| 2006/0129165 A1 | 6/2006 | Edoga et al. |
| 2006/0149137 A1 | 7/2006 | Pingleton |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0229501 A1 | 10/2006 | Jensen et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0270911 A1 | 11/2006 | Voegele et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0270882 A1 * | 11/2007 | Hjelle et al. ............ 606/108 |
| 2008/0009826 A1 | 1/2008 | Miller et al. |
| 2008/0027476 A1 | 1/2008 | Piskun |
| 2008/0097162 A1 | 4/2008 | Bonadio et al. |
| 2008/0200767 A1 | 8/2008 | Ewers et al. |
| 2008/0255519 A1 | 10/2008 | Piskun et al. |
| 2009/0012477 A1 | 1/2009 | Norton et al. |
| 2009/0093752 A1 | 4/2009 | Richard et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0326330 A1 | 12/2009 | Bonadio et al. |
| 2009/0326332 A1 | 12/2009 | Carter |
| 2009/0326461 A1 | 12/2009 | Gresham |
| 2010/0261974 A1 * | 10/2010 | Shelton et al. ............ 600/208 |
| 2010/0280326 A1 * | 11/2010 | Hess et al. ............ 600/206 |
| 2010/0280327 A1 * | 11/2010 | Nobis et al. ............ 600/210 |

FOREIGN PATENT DOCUMENTS

| | | |
|---|---|---|
| EP | 1312318 B1 | 12/2005 |
| EP | 1 774 918 A1 | 4/2007 |
| EP | 2044889 A1 | 4/2009 |
| WO | WO 93/14801 | 8/1993 |
| WO | WO 94/04067 | 3/1994 |
| WO | WO 96/36283 A1 | 11/1996 |
| WO | WO 97/33520 | 9/1997 |
| WO | WO 97/42889 | 11/1997 |
| WO | WO 99/16368 | 4/1999 |
| WO | WO 00/32120 | 6/2000 |
| WO | WO 01/49363 A1 | 7/2001 |
| WO | WO 02/07611 A2 | 1/2002 |
| WO | 2004/054456 | 7/2004 |
| WO | WO 2006/100658 A2 | 9/2006 |
| WO | WO 2008/015566 A2 | 2/2008 |
| WO | WO 2008/042005 | 4/2008 |
| WO | WO 2008/093313 A1 | 8/2008 |
| WO | WO 2008/121294 A1 | 10/2008 |

* cited by examiner

SEAL ANCHOR INTRODUCER INCLUDING BIASING MEMBER

CROSS REFERENCE TO RELATED APPLICATIONS

This application claims priority to, and benefit of, U.S. Provisional Application Ser. No. 61/263,906, filed Nov. 24, 2009, the disclosure of which is hereby incorporated by reference in its entirety.

BACKGROUND

1. Technical Field

The present disclosure relates to a seal for use in a surgical procedure. More particularly, the present disclosure relates to a seal anchor member adapted for insertion into an incision in tissue, and, for the sealed reception of one or more surgical objects such that a substantially fluid-tight seal is formed with both the tissue and the surgical object, or objects.

2. Background of Related Art

Today, many surgical procedures are performed through small incisions in the skin, as compared to the larger incisions typically required in traditional procedures. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices (e.g., trocar and cannula assemblies) or endoscopes, are inserted into the patient's body through an incision in tissue or into a naturally occurring orifice (e.g., mouth, anus, or vagina). In general, prior to the introduction of the surgical object into the patient's body, insufflation gases are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various valves and seals are used during the course of minimally invasive procedures and are widely known in the art. However, a continuing need exists for a seal anchor member that can be inserted directly into the incision in tissue and that can accommodate a variety of surgical objects while maintaining the integrity of an insufflated workspace.

SUMMARY

Disclosed herein is a seal anchor member that is adapted and configured to transition between a first state defining a first length and a second state defining a second length. In particular, the seal anchor member includes a leading portion and a trailing portion. Disposed between the leading and trailing portions is an intermediate portion that is transitionable between the first and second states. A biasing member is disposed in the intermediate portion for transitioning the intermediate portion between the first and second states. The biasing member may be a spring. The biasing member may be biased towards an expanded state. For example, subsequent to compressing the seal anchor member along the longitudinal axis, the seal anchor member may begin to transition back toward an expanded state.

The seal anchor member may include at least one longitudinally extending lumen that extends through the leading and trailing portions of the seal anchor member. The at least one lumen may be configured to receive therein an object in a substantially sealed relation. In an embodiment, the seal anchor member may include one or more lumens that are coaxial with the central longitudinal axis of the seal anchor or are parallel to the longitudinal axis of the seal anchor. The biasing member may be disposed longitudinally about the one or more lumens. In an embodiment, the biasing member may be disposed on or within an outer surface of the intermediate portion.

An example of a seal anchor member may be found in U.S. Pat. Pub. 2009/0093752, the entire contents of which are incorporated herein by reference. The various aspects of the present disclosure will be more readily understood from the following detailed description when read in conjunction with the appended figures.

BRIEF DESCRIPTION OF THE DRAWINGS

Various embodiments of the present disclosure are described hereinbelow with reference to the drawings, wherein.

DETAILED DESCRIPTION OF THE EMBODIMENTS

Figure 1:
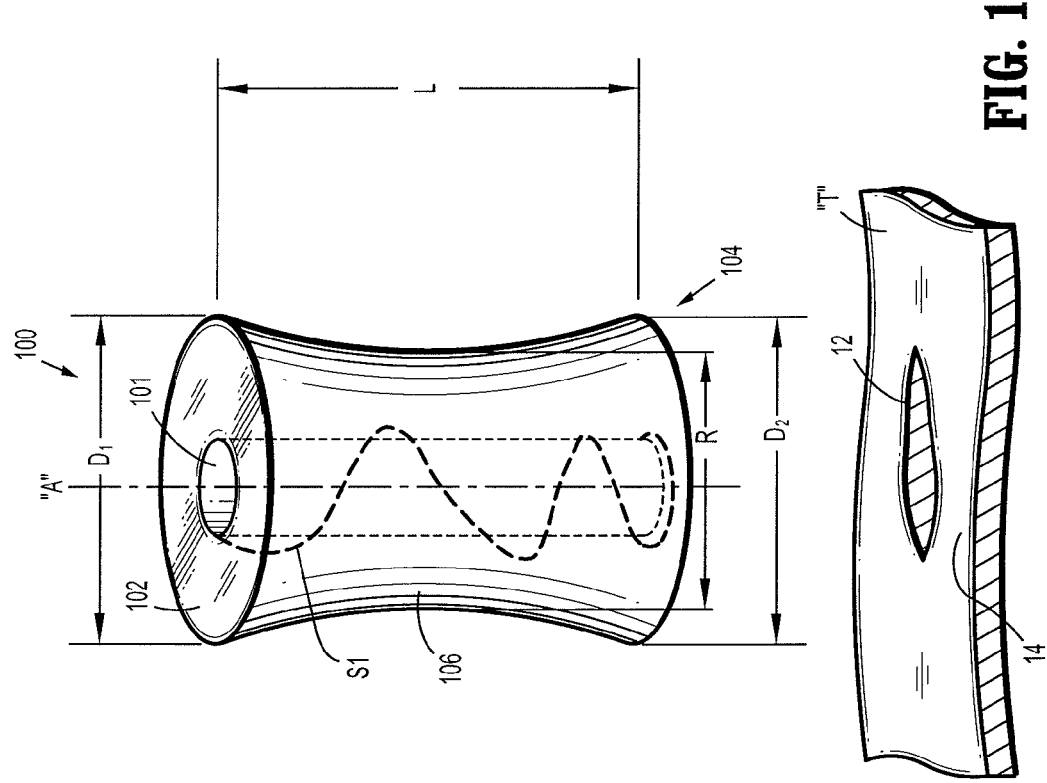
FIG. 1 is a front perspective view of a seal anchor member in accordance with the principles of the present disclosure shown in an expanded condition illustrating a seal anchor member positioned relative to body tissue.

In the drawings and in the description which follows, in which like reference numerals identify similar or identical elements, the term "proximal" will refer to the end of the apparatus that is closest to the clinician during use, while the term "distal" will refer to the end that is farthest from the clinician during use, as is traditional and known in the art.

Figure 2A:
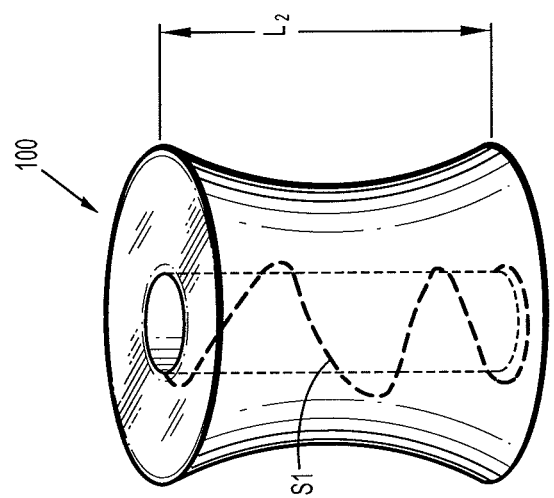
FIG. 2A is a front perspective view of the seal anchor member of FIG. 1 shown in a second state.
Figure 2:
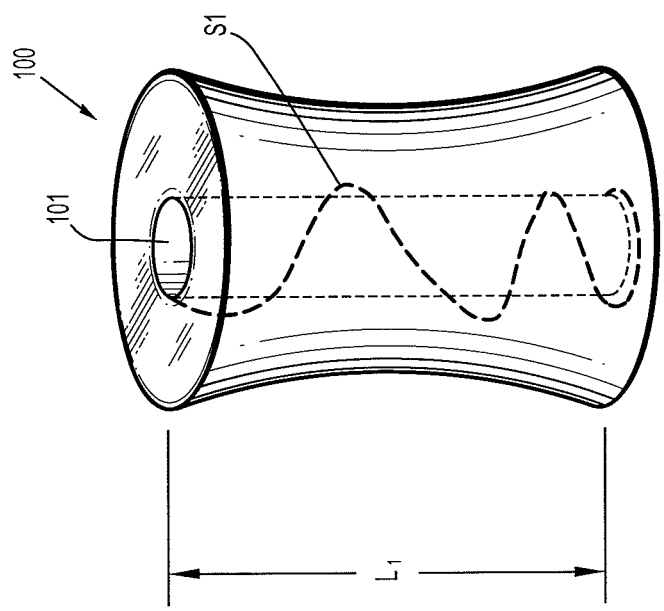
FIG. 2 is a front perspective view of the seal anchor member of FIG. 1 shown in a first state.

With reference to FIGS. 1-2A, a seal anchor member 100 for use in minimally invasive surgical procedures will now be described. The seal anchor member 100 is configured and adapted to be inserted within tissue tract 12 defined by tissue surfaces 14 formed in tissue "T", e.g., an incision or a naturally occurring orifice (e.g., mouth, anus, or vagina). Seal anchor member 100 defines a longitudinal axis "A" and has respective proximal and distal ends 102, 104 and an intermediate portion 106 disposed between the proximal and distal ends 102, 104.

As depicted in FIGS. 1-2A, proximal and distal ends 102, 104 define substantially planar surfaces. However, embodiments are also contemplated herein in which either or both of proximal and distal ends 102, 104 define surfaces that are substantially concave or convex to assist in the insertion of seal anchor member 100 within tissue tract 12. Intermediate portion 106 defines a radial dimension "R" and extends longitudinally between the proximal and distal ends 102, 104 to define an axial dimension or length "L". As shown in FIGS. 1-2A, the radial dimension "R" of intermediate portion 106 varies along the length "L", i.e., the cross-sectional dimension may vary long length "L", to facilitate anchoring of the seal anchor member 100 within tissue "T". However, in an embodiment of the seal anchor member 100, the radial dimension "R" may remain substantially uniform along the length "L".

The radial dimension "R" of intermediate portion 106 is appreciably less than the respective diameters D1, D2 of proximal and distal ends 102, 104 such that seal anchor member 100 defines an "hour-glass" shape or configuration to assist in anchoring seal anchor member 100 within tissue "T". However, in an alternate embodiment, the radial dimension "R" of intermediate portion 106 may be substantially equivalent to the respective diameters D1, D2 of proximal and distal ends 102, 104. In cross-section, intermediate portion 106 may exhibit any suitable configuration, e.g., substantially circular, oval, or oblong.

Seal anchor member 100 includes a port 101 disposed about a central longitudinal axis "A" and will be described in more detail below. It is to be understood that in alternative embodiments, port 101 may be positioned differently, e.g., not coaxial about central longitudinal axis "A" and the seal anchor member 100 may include a plurality of ports. In addition, the seal anchor 100 may be devoid of any port.

Port 101 in the absence of a surgical object inserted therein is configured and adapted to prevent the escape of insufflation gas through the port 101. For example, the port 101 may be a slit extending the longitudinal length of the seal anchor member 100 through the proximal and distal ends 102, 104. Alternatively, port 101 may define an opening within the seal anchor member 100 having an initial open state having a first inner dimension and upon the introduction of a surgical object, the port 101 transitions to a second state having a second inner dimension configured and adapted to accommodate the surgical object such that a substantially fluid-tight seal is formed therewith by substantially approximating the size and shape of the surgical object to inhibit the escape of insufflation gas through the port 101 in the presence of the surgical object.

The seal anchor member 100 is configured and adapted to transition between a first state (FIG. 2) and a second state (FIG. 2A) to facilitate insertion of the seal anchor member 100 within tissue "T". As shown in FIGS. 1-2A, the seal anchor member 100 includes a biasing member "S1", e.g., a spring, that facilitates the transition between a first expanded state shown in FIG. 2 in which the seal anchor member 100 has a length L1 and a second collapsed state shown in FIG. 2A in which the seal anchor member 100 has a length L2. The biasing member "S1" is biased towards the expanded state as shown in FIG. 2. A surgeon may collapse the seal anchor member 100 such that the seal anchor member 100 has a collapsed length L2. Subsequent to insertion of the seal anchor member 100, biasing member S1 will facilitate transition back to the expanded condition in which the seal anchor member has a length L1. The seal anchor member 100 will therefore transition toward the expanded condition. The biasing member "S1" is positioned within the seal anchor member 100 such that the biasing member "S1" does not interfere with the function of port 101. It is noted that in other embodiments, the seal anchor member 100 may be biased toward a collapsed state.

Figure 3A:
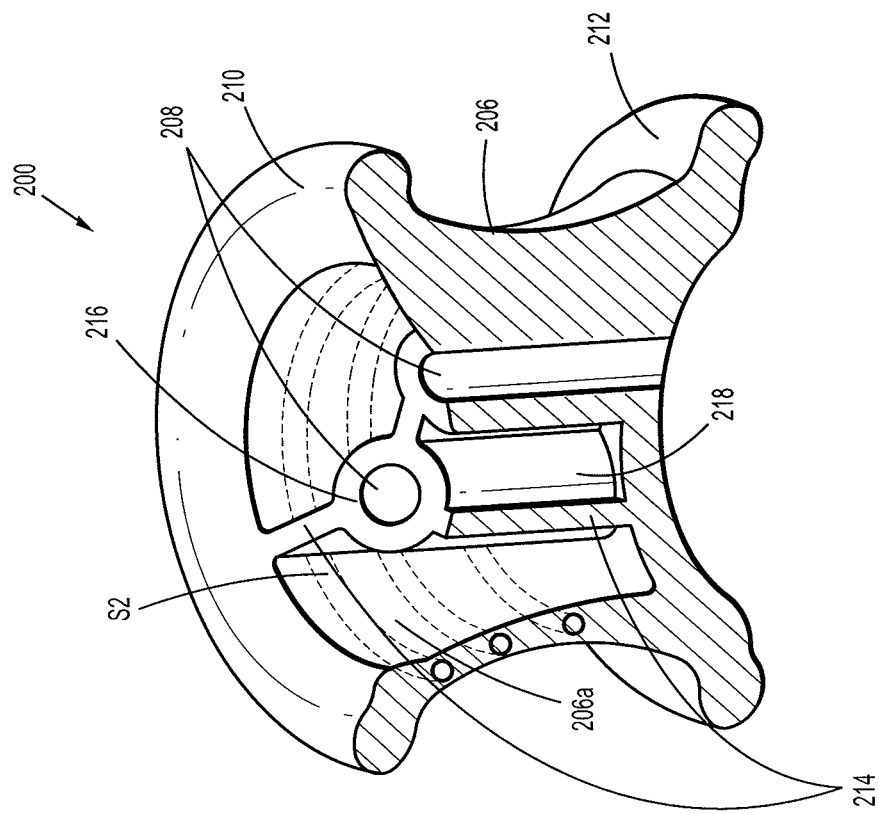
FIG. 3A is a cross-sectional view of the seal anchor member taken along section line 3A-3A of FIG. 3.
Figure 3:
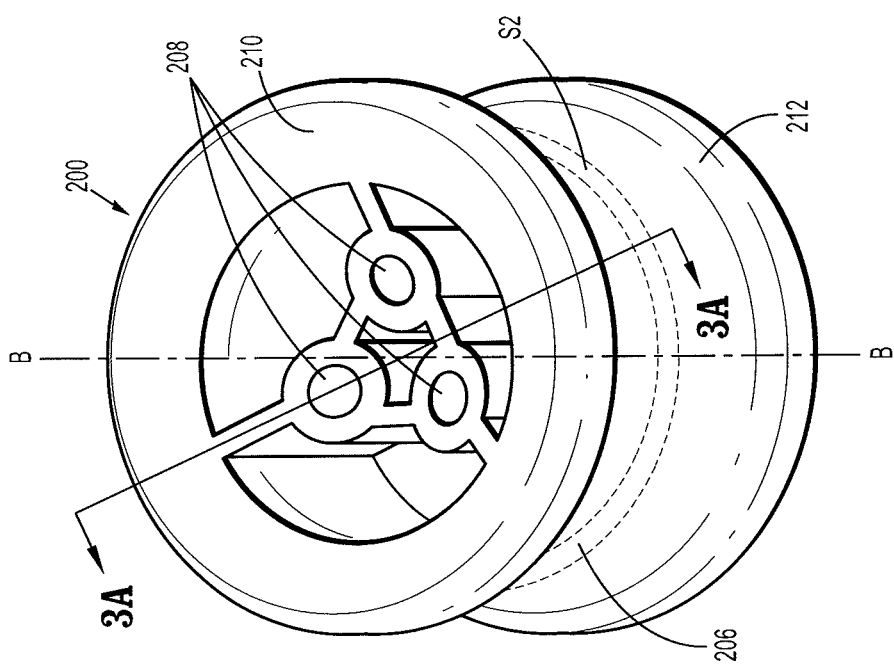
FIG. 3 is a top perspective view of an embodiment of a seal anchor member.

In an alternative embodiment shown in FIGS. 3-3A, a seal anchor member 200 having an intermediate portion 206 is shown. A biasing member "S2" may be disposed on or within a surface 206a, i.e., the outer wall, of an intermediate portion 206 extending between proximal rim (trailing end) 210 and distal rim (leading end) 212. Biasing member "S2" is configured and adapted to be biased in a direction along longitudinal axis "B" to facilitate a transition between an expanded first state and a collapsed second state. The seal anchor member 200 may include a plurality of ports 208 secured to the intermediate portion 206 by connective members 214 such that the longitudinal portion of the ports 208 remain substantially constant with respect to the respective proximal and distal rims 210, 212 during insertion and removal of the surgical object.

It is contemplated that biasing members S1, S2 may be formed from any material and have any configuration such that biasing members S1, S2 will have an internal biasing force. For example, biasing members S1, S2 may be a coiled wire and may be formed from a shape memory material, e.g., nitinol, such that biasing members S1, S2 provide a bias in a particular direction to facilitate either the compression or expansion of seal anchor members 100, 200.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

The invention claimed is:

1. A seal anchor member comprising:
   a leading portion;
   a trailing portion;
   an intermediate portion disposed between the leading and trailing portions and including an outer wall having an inner surface and an outer surface, the intermediate portion transitionable between a first state defining a first length and a second state defining a second length;
   at least one lumen longitudinally extending between the leading and trailing portions having an outer surface and an inner surface; and
   a biasing member disposed around the outer surface of the lumen for transitioning the intermediate portion between the first and second states, wherein the biasing member is disposed between the inner surface and the outer surface of the outer wall of the intermediate portion in a helical pattern surrounding the lumen, and wherein the biasing member is biased toward a fully expanded state.

2. The seal anchor of claim 1, wherein the biasing member is a spring.

3. The seal anchor of claim 1, wherein the at least one lumen is configured to receive an object therein, the object being in a substantially sealed relationship with the inner surface of the lumen.

4. The seal anchor of claim 1, wherein the at least one lumen is coaxial with a central longitudinal axis of the intermediate portion.

5. The seal anchor of claim 1, wherein the intermediate portion has an inner wall and outer wall such that the biasing member is disposed therebetween.

6. A seal anchor member comprising:
   a leading portion;
   a trailing portion, at least one of the leading portion and the trailing portion defined by a radially outward rim;
   an intermediate portion disposed between the leading and trailing portions, the intermediate portion transitionable between a first state defining a first length and a second state defining a second length;
   at least one port longitudinally extending between the leading and trailing portions having an initial open state having a first inner dimension; and a biasing member disposed around the port for transitioning the intermediate portion between the first and second states, wherein the biasing member is disposed in a helical pattern on an outer surface of the port, and wherein the biasing member is biased toward a fully expanded state.

7. The seal anchor of claim 6, wherein upon introduction of an object the port transitions from the first inner dimension to a second state having a second inner dimension configured to accommodate the object such that a substantially fluid-tight seal is formed therewith.

8. The seal anchor of claim 7, wherein the biasing member is a spring.

9. The seal anchor of claim 7, wherein two ports are secured to the intermediate portion by at least two connective members.

10. The seal anchor of claim 1, wherein the biasing member has a first end and a second end opposing the first end, wherein the first end is operably coupled to a trailing end of the lumen and the second end is operably coupled to a leading end of the lumen.

11. The seal anchor of claim 6, wherein the biasing member has a first end and a second end opposing the first end, wherein the first end is operably coupled to a trailing end of the port and the second end is operably coupled to a leading end of the port.

12. The seal anchor of claim 6, wherein the rim is configured as a flange.

13. The seal anchor of claim 6, wherein both the leading portion and the trailing portion are defined by a rim.

14. The seal anchor of claim 6, wherein the rim is disposed radially outward with respect to the intermediate portion.

\* \* \* \* \*